United States Patent [19]

Li et al.

[11] 4,277,410

[45] Jul. 7, 1981

[54] PROCESS FOR THE PRODUCTION OF CARBOXYLIC AMIDES USING ALKYLTIN CATALYSTS

[75] Inventors: Thomas Z. Li; James Lamont, both of Cincinnati, Ohio

[73] Assignee: Emery Industries, Inc., Cincinnati, Ohio

[21] Appl. No.: 145,925

[22] Filed: May 2, 1980

[51] Int. Cl.³ .............................. C09F 5/00; C11C 3/00
[52] U.S. Cl. ................................... 260/404; 260/404.5; 564/131; 564/141
[58] Field of Search .................. 260/404, 404.5 R; 564/139, 141

[56] References Cited

U.S. PATENT DOCUMENTS

| | | | |
|---|---|---|---|
| 2,013,108 | 9/1935 | Reppe et al. | 260/404 |
| 3,674,851 | 7/1972 | Senoo et al. | 561/141 |
| 3,801,610 | 4/1974 | Werdehausen | 260/404 |
| 3,816,483 | 6/1974 | Werdehausen | 260/404 |

*Primary Examiner*—John F. Niebling
*Attorney, Agent, or Firm*—Kenneth D. Tremain

[57] ABSTRACT

An improved process is provided for the amidation of carboxylic acids. For the process a carboxylic acid is reacted with ammonia gas at an elevated temperature and at atmospheric pressure or above in the presence of an alkyltin catalyst, preferably an alkyltin compound containing both hydroxyl and halo groups. High conversions are achieved with the process and the resulting products have low nitrile contents.

8 Claims, No Drawings

PROCESS FOR THE PRODUCTION OF CARBOXYLIC AMIDES USING ALKYLTIN CATALYSTS

BACKGROUND OF THE INVENTION

Numerous methods are known for the production of carboxylic amides by reaction of the corresponding carboxylic acid, anhydride or lower alkyl esters thereof with ammonia. While these reactions can be accomplished in the absence of catalyst at elevated temperature and very high pressures (see U.S. Pat. No. 3,253,006) the trend has been to the use of processes which do not require the use of high pressure and which still provide high conversion with high selectivity to the desired amide product. Accordingly, catalytic procedures have been developed whereby the reaction of the carboxylic moiety with ammonia can be achieved by substantially reduced pressures and, in some cases, even at atmospheric pressure.

One such atmospheric amidation process is described in U.S. Pat. No. 2,013,108 and involves passing gaseous ammonia into the fatty acid melt which contains a surface catalyst. Useful surface catalysts for the process are solid inorganic substances such as bleaching earths, fuller's earth, silica gel, natural or synthetic zeolites, oxides and phosphates of aluminum, thorium, tungsten, cerium, praseodymium, neodymium, and lanthanum, bauxite, charcoal, activated carbon, pumice, and the like. With this process it typically requires forty-eight or more hours to achieve acceptable levels of conversion and, as a result, some of the amide is dehydrated to the corresponding nitrile.

Since the yield of the desired amide product can be significantly reduced by this competing reaction, i.e. dehydration of the amide to nitrile, long reaction times generally cannot be tolerated. Accordingly, processes requiring shorter reaction times and employing reaction conditions which minimize undesirable by-product formation have been developed. One such process for the production of carboxylic acid amides is disclosed in U.S. Pat. No. 3,816,483. The process can be conducted at atmospheric pressure and, as a result of the shorter reaction times required, the formation of undesirable nitrile by-product is reduced. Reaction of the carboxylic acid and ammonia is acccomplished in the presence of a reaction-soluble catalyst of a Group IVb or Vb metal, preferably a compound of titanium, zirconium or tantalum.

SUMMARY OF THE INVENTION

We have now discovered an improved process for the production of carboxylic amides which utilizes alkyltin catalysts. With the process of this invention high conversions with high selectivity to the desired amide product are obtained with short reaction times and at low catalyst levels. Additionally, the process can be carried out at atmospheric pressure while still obtaining acceptable reaction rates and products having low acid values and low nitrile contents. Amides obtained by the process are useful additives for a wide variety of polymeric materials.

For the process 0.1 to 10 wt. percent and, more preferably, 0.25 to 4 wt. percent alkyltin catalyst is employed. Useful alkyltin catalysts have the formula $RSnX_3$ or $R_2SnX_2$ where R represents a hydrocarbon radical of from 1 to 12 carbon atoms and X represents a hydroxyl, halo or carboxylate group. Preferably R is an alkyl group having from 1 to 4 carbon atoms and X is halogen and hydroxyl.

Aliphatic, cycloaliphatic and aromatic carboxylic acids having from about 6 to 24 carbon atoms can be employed in the process. Carboxylic acids having a plurality of carboxyl groups can also be amidated in accordance with this process, however, the invention is particularly useful for the amidation of aliphatic monocarboxylic acids having 8 to 22 carbon atoms or mixtures thereof. While the process can be conducted at temperatures as high as 250° C. and under high pressure it is most preferably carried out at a temperature between 110° and 220° C. and at atmospheric pressure or up to about 100 psi. Ammonia gas is employed for the reaction.

DETAILED DESCRIPTION

The improved process of this invention can be used for the amidation of a wide variety of aliphatic, cycloaliphatic or aromatic carboxylic acids containing from about 6 to 24 carbon atoms. While the process is particularly useful with monocarboxylic acids, it is equally adaptable for use with di- and higher polycarboxylic acids. When compounds containing a plurality of carboxyl groups are used, all or a portion of the carboxyl functionality may be converted to the amide. Cycloaliphatic acids which can be employed include cyclopentanecarboxylic acid, cyclohexanecarboxylic acid, cyclohexanedicarboxylic acid, abietic acid, camphoric acid and the like. Illustrative aromatic carboxylic acids which can be amidated in accordance with the present process include benzoic acid, naphthoic acid, the toluic acids, chlorobenzoic acid, anisic acid, phenylacetic acid, hydrocinnamic acid, cinnamic acid, phthalic acid or anhydride, diphenic acid and the like. Typical aliphatic acids which can be utilized in the process are caproic acid, caprylic acid, capric acid, lauric acid, myristic acid, myristoleic acid, palmitic acid, palmitoleic acid, stearic acid, isostearic acid, oleic acid, linoleic acid, elaidic acid, linolenic acid, eleostearic acid, arachidic acid, behenic acid, erucic acid, lignoceric acid, nervonic acid, ricinoleic acid, azelaic acid, sebacic acid, brassylic acid and the like.

The process is particularly useful for the amidation of aliphatic monocarboxylic acids having from 8 to 22 carbon atoms. These fatty acid amides are used throughout the plastics industry as additives for thermoplastic resins and function as lubricants, release agents, slip agents, antiblock agents, and the like. These aliphatic carboxylic acids can be branched- or straight-chain, saturated or unsaturated, and they can be used alone or, as is more typically the case, present as mixtures. Useful mixtures of fatty acids for this purpose are obtained from triglycerides present in natural fats and oils. For example, fatty acids obtained from coconut oil, cottonseed oil, linseed oil, palm oil, soya oil, tall oil, safflower oil, corn oil, rapeseed oil or animal fats and oils are advantageously used. In addition to acids derived from natural sources synthetic fatty acids, such as those obtained by the oxidation of paraffins or from oxo processes, can also be advantageously used for the process.

In addition to the forementioned acids, esters and anhydrides of the acids can also be utilized in the process. When esters are employed, alkylated amides can result.

The improvement in the process of this invention results from the use of specific alkyltin catalysts. Alkyltin catalysts useful for the process correspond to the general formulae

and

where R represents a hydrocarbon radical having from one up to about 12 carbon atoms and X represents a radical selected from the group consisting of hydroxyl, halo or carboxylate. R can be an alkyl, aryl, cycloalkyl, alkaryl or aralkyl group but is preferably an alkyl moiety, which can be either straight-chain or branched, containing from 1 to 4 carbon atoms. Halo moieties of particular interest are chloro and bromo. Useful carboxylate radicals are generally derived from lower aliphatic acids and preferably contain from 2 to 6 carbon atoms.

In a preferred embodiment of this invention, the alkyltin compound contains two different X radicals of the aforementioned types. The presence of both halo and hydroxyl groups has been found to be particularly advantageous and excellent results are obtained using alkyltin catalysts of the formula $RSn(OH)_2X$ where R is hydrocarbon radical as previously defined and X is bromo or chloro. Especially useful compounds of this type are those where X is chloro and R is a $C_{1-4}$ alkyl. Such compounds are commercially available and are disclosed in U.S. Pat. No. 3,480,655.

Illustrative alkyltin compounds useful for the present process include methyltin trichloride, methyltin tribromide, dimethyltin dichloride, butyltin trichloride, dibutyltin dichloride, dibutyltin diacetate, butylchlorotin dihydroxide, dibutylchlorotin hydroxide and the like.

The amount of the alkyltin catalyst can be widely varied depending on the reaction conditions employed and the particular fatty acid or fatty acid derivative being reacted. The amount of catalyst used can range from 0.1 to 10% by weight based on the fatty acid, however, most generally it will be between 0.25 and 4 percent by weight—particularly when the catalyst is one of the preferred alkylchlorotin hydroxide compounds.

Employing the alkyltin catalysts of this invention it is possible to achieve highly efficient amidation of the carboxylic acids. High conversions are obtained with high selectivity to the desired amide and minimal formation of undesirable nitrile by-product. Employing typical prior art catalysts it is extremely difficult, and in some instances virtually impossible, to drive the reaction during the final stages of reaction. When the acid value reaches about 10 the reaction stalls so that excessive reaction time and/or heating are required to get the acid value to 3 or below. It may even be necessary to add additional catalyst during the final stages of the prior art reactions. As a result of the severe conditions necessary during the latter stages of the reaction, excessive dehydration of the amide can occur resulting in higher than desired nitrile contents and other undesirable side reactions can also occur. Employing the alkyltin catalysts of this invention it is possible to effectively and rapidly achieve the desired low acid values without requiring excessive reaction times or temperatures thereby minimizing the formation of nitrile and the other problems associated therewith.

A further advantage of the present process lies in the ability to produce amides having improved stability. Typically, some catalyst residue will remain in the amide unless extensive purification, which is prohibitively expensive for commercial operations, is undertaken. While the amount of catalyst residue is small, it can nevertheless promote degradation and lead to product instability if the material is stored for prolonged periods and/or at elevated temperatures. These catalyst residues can also present stability problems in polymeric resins formulated with the amides. With the products of this invention prepared using the alkyltin catalysts improved stability is observed.

Process conditions and other operational details can be widely varied. The reaction temperature will generally be between about 100° C. and 220° C., however, temperatures as high as 250° C. can be used. As will be evident to those skilled in the art, reaction temperatures which are too low require excessive reaction times whereas, if the temperature is too high, undesirable side reactions will occur. For the process of this invention using the alkyltin catalysts it is preferred that the temperature be in the range 140° C. to 190° C. Employing temperatures in this range it is possible to achieve good conversion with minimal nitrile formation while still obtaining acceptable reaction rates.

The reaction may be carried out at atmospheric pressure or pressure up to several thousand psi may be employed. It is a particularly preferred aspect of the invention, however, that the process by conducted at atmospheric or at moderate pressure up to about 100 psi. By such operation the use of costly high pressure equipment is avoided.

Gaseous ammonia is utilized for the reaction—the amount depending on the particular method of operation. Generally, about 3 to 4.5 moles ammonia is employed per mole of carboxylic acid. When the reaction is conducted at atmospheric pressure about 0.4 to 2 SCFH (air rotameter) ammonia per kilogram carboxylic acid is subsurfacely introduced into the reaction mixture. Excess ammonia may be recycled. While it is not necessary to dry the ammonia or reactant(s), excessive amounts of water should not generally be present therein. The process is usually conducted as a batch operation, however, it may be carried out on a continuous or semi-continuous basis. An inert solvent may be used in carrying out the process but is not necessary.

The reaction is conveniently followed by periodically removing samples from the reaction mixture and determining the acid value. It is generally desired that the reaction be continued until an acid value of 5 or below is achieved. Using the alkyltin catalysts of this invention, it is possible to readily achieve acid values less than 2 in short reaction times without the formation of excessive amounts of undesirable nitrile by-products.

In view of the small amount of the alkyltin catalyst employed and the fact that the presence of the catalyst does not significantly detract from the stability of the amide or resinous products formulated therewith, the amide product can be removed from the reactor at the termination of the reaction and used as such. It is more customary, however, to subject the reaction product to a stripping operation or fractional distillation prior to use. Also, amides produced by the process of this invention may be treated to even further reduce the acid value in accordance with known procedures such as that described in U.S. Pat. No. 3,920,523.

The alkyltin catalysts may also be employed in conjunction with other compounds known to promote amidation and enhance the reaction rate, inhibit nitrile formation, improve color or achieve other desirable results in the process. For example, it may be advantageous to include a small amounts of alkali metal phosphate or alkali metal hydroxide with the alkyltin compound. However, the amounts of such compounds will typically not exceed about 2 percent, based on the weight of the carboxylic acid.

The following examples illustrate the process of this invention more fully. In these examples all percentages are on a weight basis unless otherwise indicated.

EXAMPLE I

To demonstrate the improved process of this invention utilizing alkyltin catalysts and the ability to obtain high conversions while carrying out the amidation at atmospheric pressure, the following reaction was conducted: Erucic acid (500 gms.) was added to a one-liter glass reaction vessel equipped with a stirrer, condenser with water trap, thermometer and subsurface gas inlet. The reactor and its contents were heated to 40°–60° C. and 2.5 gms butylchlorotin dihydroxide (0.5 wt. %) added. The temperature was then increased and maintained at 165°–170° C. while ammonia gas was introduced subsurfacely at a rate of 0.5 SCFH (air rotameter). 98.2 Percent conversion of the erucic acid was obtained after 11 hours and the final product (acid value 2.9) contained 95% erucamide.

A portion of the product was treated to further reduce the acid value. This was accomplished by alkali refining with 1% excess (based on the acid value) trisodium phosphate. The treated product (after filtering through dicalite) had an acid value of 0.52. Both the original (untreated) product and the product obtained after alkali refining were effective slip agents when incorporated into low density polyethylene at 0.15 weight percent level. The kinetic coefficient of friction of the polyethylene film is significantly reduced by the addition of as little as 0.02 wt. % of the erucamide product.

EXAMPLE II

To demonstrate the versatility of the present improved process, the reaction of Example I was repeated except that the amidation was conducted under pressure. For this reaction 810 gms erucic acid containing 0.5 wt. % butylchlorotin dihydroxide was charged to a 2 liter Parr autoclave, the reactor purged several times with gaseous ammonia and then heated and maintained at 165° C. while maintaining a constant pressure of 30–35 psi within the autoclave by the addition of ammonia. The vent of the autoclave was slightly cracked to permit water formed during the reaction to escape. An acid value of 1.8 was obtained after 15.5 hours. Conversion of erucic acid was 98.9%.

EXAMPLE III

Example II was repeated except that 8.1 gms. $Na_3PO_4.12H_2O$ was added with the butylchlorotin dihydroxide catalyst. After 11 hours 99.5% conversion was obtained and the final product had an acid value of only 0.65.

EXAMPLE IV

In accordance with the procedure of Example II erucamide was prepared as follows: 800 gms. erucic acid was combined with 4.0 gms. butylchlorotin dihydroxide, 5.6 gms. $Na_3PO_4.12H_2O$, 2.4 gms. LiOH and reacted with ammonia at a pressure of 30–35 psi. The acid value of the reaction mixture was reduced to about 10 hours reaction. With further reaction, an acid value of 0.9 was achieved without significantly increasing the nitrile content of the final product.

EXAMPLE V

A diamide was obtained by the amidation of azelaic acid at atmospheric pressure. For this reaction 600 gms. azelaic acid was combined with 3 gms. butylchlorotin dihydroxide and 6 gms. $Na_3PO_4.12H_2O$. The reaction mixture (acid value 596.8) was heated to 175° C. and gaseous ammonia bubbled in at a rate of 0.5 SCFH. When the acid value was reduced to about 20 (approx. 15 hours) the reaction was terminated. Greater than 96% conversion of the carboxyl functionality was obtained with high selectivity to the desired amide product.

EXAMPLE VI

Dimethyltin dichloride was employed as the catalyst for the amidation of erucic acid in accordance with the procedure of Example I. For the reaction 450 gms. erucic acid was combined with 2.25 gms. dimethyltin dichloride and reacted with ammonia at 170° C. for about 18 hours. The crude erucamide obtained from the reaction had an acid value of 2.2 with low nitrile content and was a useful slip agent for polyolefin polymers.

EXAMPLE VII

Erucamide was prepared as follows: Erucic acid (450 gms.) was reacted with ammonia at atmospheric pressure at a temperature of 168°–170° C. in the presence of 0.5 wt. percent butyltin trichloride catalyst. After 12.5 hours the acid value of the reaction mixture was 2.98 and the reaction was terminated. High conversion (greater than 95%) of the erucic acid was obtained and the erucamide had good color and nitrile content less than 5%.

EXAMPLE VIII

In a manner similar to that described in Example I, erucic acid was reacted with ammonia in the presence of 0.5 wt. percent dibutyltin diacetate catalyst. Greater than 98 percent conversion was obtained and the resulting product had an acid value of 2.2 with low nitrile content. Similar conversions with high selectivity to the desired amide product are obtained at catalyst levels of 0.25–2 percent.

EXAMPLE IX

To demonstrate the ability to carry out the process at lower catalyst levels and the ability to make the catalyst additions incrementally, the following reaction was conducted: Erucic acid (1076 gms.) containing 0.2 wt. percent butylchlorotin dihydroxide was charged to a reaction vessel and heated to 165°–175° C. while introducing ammonia gas subsurfacely at a rate of 0.5–0.75 SCFH. After about 7 hours, when the acid value of the mixture had been lowered to 43.9, additional butylchlorotin dihydroxide (0.1 wt. percent) was added. The reaction was continued for an additional 9 hours during which time the acid value was reduced to 2.5. Conversion of erucic acid was 98 percent and the erucamide had good color and low nitrile content.

EXAMPLE X

Elaidic acid was converted to the amide in accordance with the procedure of Example I. For the reaction 0.5 wt. percent butylchlorotin dihydroxide was employed with 1% trisodium phosphate. The crude elaidamide had an acid value of 1.5 and total amide content of 96.1%.

EXAMPLE XI

Oleic acid (1058 gms.) was reacted with ammonia at 165° C. and 35 psi in the presence of 0.5 wt. percent butylchlorotin dihydroxide and 1% trisodium phosphate. High conversion (95%) of the oleic acid was obtained in 11 hours with high selectivity to the desired amide product. The final product had an acid value of 1.8.

EXAMPLE XII

To demonstrate the ability to conduct the amidation in an inert reaction medium 400 gms. benzoic acid was dissolved in 400 mls. mineral spirits with 2 gms. butylchlorotin dihydroxide. The solution was then heated with agitation to 165° C. while introducing ammonia below the surface of the liquid through a dispersion tube at a rate of 0.5 SCFH. As the reaction progressed the amide product came out of solution. An acid value of 12 was achieved after only 7 hours reaction. At the completion of the reaction the insoluble amide product was recovered by filtration, washed and dried. Benzamide (melt point 133°-135° C.) obtained by this process is substantially free of undesirable nitrile by-product.

EXAMPLE XIII

To demonstrate the superior results obtained by the process of this invention, as compared to results obtained following the process of U.S. Pat. No. 3,816,483, the following comparative experiments were conducted. For all of these reactions 500 gms. erucic acid was employed. The reactions were conducted at atmospheric pressure.

In the first set of reactions the temperature was maintained at 170° C. while introducing ammonia below the surface of the reaction mixture at a rate of 0.5 SCFH (air rotameter). For the first reaction (Experiment A) 0.5 wt. percent butylchlorotin dihydroxide was employed as the catalyst whereas in the second reaction (Experiment B) 0.5 wt. percent tetraisopropyl titanate, one of the preferred catalysts of U.S. Pat. No. 3,816,483, was used. The rates of reaction were comparable and in both instances acid values less than 3 were obtained in 11-12 hours. Quite unexpectedly, however, the nitrile content (as determined by vapor phase chromatographic analysis) was significantly lower with the product prepared using the butylchlorotin dihydroxide. Whereas the product of Experiment B contained 8.0 percent nitrile, the nitrile content of the product of Experiment A was only 5.4%. This represents a significant and highly desirable improvement for the product obtained in accordance with the process of this invention.

To further demonstrate the advantages of the use of the alkyltin catalysts of this invention and the improved result obtained, two reactions were conducted in accordance with the procedure of Example I of U.S. Pat. No. 3,816,483. For these reactions the temperature was maintained at 165° C. and the ammonia introduced subsurfacely at a rate of about 4.5 SCFH (air rotameter), which is approximately equivalent to 100 liters/hour, for two hours and then at a rate of about 3.5 SCFH, which is approximately equivalent to 75 liters/hour, for the remainder of the reaction. Butylchlorotin dihydroxide (1 wt. %) was employed as the catalyst for the first reaction (Experiment C) and 1.0 wt. percent tetraisopropyl titanate was used for other reaction (Experiment D). Both reactions were taken to acid values less than 3 and the products recovered. The product of Experiment D had a 25% higher nitrile content than the product of Experiment C, obtained in accordance with the present process.

In addition to the ability to obtain substantially lower nitrile contents, other advantages are obtained by the process of this invention. Products obtained in accordance with the present process exhibit improved heat stability. To demonstrate this 200 gms. product A and 200 gms. product B were heated in glass containers at 125° C. After 24 hours, 48% change in transmission was obtained with product A whereas 56% change in transmission was obtained with product B. Transmission was measured at 550 m$\mu$ on a solution of 1 gram of the material in 25 cc isopropyl alcohol.

$$\% \text{ change} = \frac{T_i - T_f}{T_i} \times 100$$

After 48 hours, 65% change in transmission was observed for product A and 79% change was obtained for product B.

Heat stabilities of formulated resins containing the above-prepared erucamide products (A-D) were also determined. For these studies 100 gms. PVC resin (Geon 102 EPF-5) was blended with 50 gms. dioctylphthalate and 3 gms. erucamide. The mixture was milled at 360° F. for 3 minutes to obtain a sheet having a thickness of 35 mils. Water-white films were obtained in all instances. Samples were then placed in a 375° F. oven and observed for discoloration at five minute intervals. A noticeable pinkish cast developed in the resin formulated with the products B and D after only 10 minutes whereas first evidence of discoloration did not occur with the resins formulated with products A and C until after 15 minutes.

The amide products obtained by the process of the present invention and having the above-described improved properties can be used in any of the known applications where amides are typically employed. For example, amides of fatty acids, particularly unsaturated fatty acids such as oleic acid and erucic acid, are useful as slip and antiblock agent for polyethylene and other polyolefins. The incorporation of small amounts of these amides significantly reduces the kinetic coefficient of friction of these polymers and facilitates one film sliding over another and reduces the tendency of one film to adhere to another. The incorporation of 20-2000 ppm of such amides will generally suffice for this purpose, however, larger amounts of the amides may be incorporated into polyolefins and other polymers to impart other desirable properties. In addition to being useful in the formulation of resins, amides obtained by the process of this invention may be used in waxed and resin-coated papers. These amides can also be employed as blending agents to improve the solubility of synthetic resins, such as polyamides, in waxes; as additives in cosmetic formulations; as dispersants in printing inks; and as lubricants.

We claim:

1. An improved process for the preparation of amides which comprises reacting an aliphatic, cycloaliphatic or aromatic carboxylic acid containing from 6 to 24 carbon atoms, or ester or anhydride thereof, with ammonia at a temperature of 100° C. to 220° C. in the presence of 0.1 to 10 wt. percent, based on the carboxylic acid, of a alkyltin catalyst of the formula $RSnX_3$ or $R_2SnX_2$ where R is a hydrocarbon radical having from 1 to 12 carbon atoms and X is hydroxyl, halo or carboxylate having from 2 to 6 carbon atoms.

2. The process of claim 1 wherein the reaction is conducted at atmospheric pressure.

3. The process of claims 1 or 2 wherein the carboxylic acid is an aliphatic carboxylic acid or mixture of carboxylic acids having from 8 to 22 carbon atoms.

4. The process of claim 3 wherein the reaction temperature is 140° C. to 190° C. and the alkyltin catalyst is present in an amount from 0.25 to 4 wt. percent, based on the carboxylic acid.

5. The process of claim 4 wherein the alkyltin compound has the formula $RSn(OH)_2X$ where R is a $C_{1-4}$ alkyl group and X is bromine or chlorine.

6. The process of claim 5 wherein about 3 to 4.5 mols ammonia is employed per mol carboxylic acid.

7. The process of claim 6 wherein the alkyltin catalyst is butylchlorotin dihydroxide.

8. A process for the preparation of erucamide which comprises reacting ammonia with erucic acid at a temperature of 140° C. to 190° C. and at a pressure from atmospheric up to about 100 psi in the presence of an alkyltin catalyst of the formula $RSn(OH)_2X$ where R is a $C_{1-4}$ alkyl group and X is bromine or chlorine, said catalyst present in an amount from 0.25 to 4 wt. percent, based on the erucic acid, and employing 3 to 4.5 mols ammonia per mol erucic acid.

* * * * *